US012593999B2

(12) United States Patent
Wang et al.

(10) Patent No.: US 12,593,999 B2
(45) Date of Patent: Apr. 7, 2026

(54) METHOD AND APPARATUS FOR MEASURING BRAIN FREE WATER CONTENT AND MRI SYSTEM

(71) Applicants: Siemens Healthineers Ltd., Shanghai (CN); Henan Provincial People's Hospital, Zhengzhou (CN)

(72) Inventors: Mei Yun Wang, Zhengzhou (CN); Xian Chang Zhang, Beijing (CN); Yan Bai, Zhengzhou (CN); Rui Zhang, Zhengzhou (CN); Ru Shi Chen, Zhengzhou (CN)

(73) Assignees: Siemens Healthineers Ltd., Shanghai (CN); Henan Provincial People's Hospital, Zhengzhou (CN)

( * ) Notice: Subject to any disclaimer, the term of this patent is extended or adjusted under 35 U.S.C. 154(b) by 706 days.

(21) Appl. No.: 17/876,734

(22) Filed: Jul. 29, 2022

(65) Prior Publication Data

US 2023/0038549 A1 Feb. 9, 2023

(30) Foreign Application Priority Data

Jul. 30, 2021 (CN) .......................... 202110878454.9

(51) Int. Cl.
*A61B 5/055* (2006.01)
*G01R 33/44* (2006.01)
(Continued)

(52) U.S. Cl.
CPC ............ *A61B 5/055* (2013.01); *G01R 33/448* (2013.01); *G01R 33/4828* (2013.01); *G01R 33/50* (2013.01); *G01R 33/543* (2013.01)

(58) Field of Classification Search
None
See application file for complete search history.

(56) References Cited

U.S. PATENT DOCUMENTS

2019/0353718 A1 11/2019 Griswold et al.

FOREIGN PATENT DOCUMENTS

CN 111090069 A 5/2020

OTHER PUBLICATIONS

Oros-Peusquens et al. ("a single scan rapid whole brain protocol for quantitative water content mapping with neurobiological implications") (Year: 2019).*

(Continued)

*Primary Examiner* — Michael J Carey
*Assistant Examiner* — Marjan Saboktakin
(74) *Attorney, Agent, or Firm* — Banner & Witcoff, Ltd.

(57) ABSTRACT

In a method for measuring brain free water content, in response to an RF excitation field generated on the basis of a magnetic resonance fingerprinting sequence and applied to the brain, an equilibrium magnetization mixed term (M0) signal is acquired from radiation emitted by each excited voxel of the brain, to obtain an M0 value of each voxel of the brain; a receive coil sensitivity (RP) value of each voxel of the brain is acquired; the M0 value of each voxel of the brain is divided by the RP value of the corresponding voxel to obtain a proton density (PD) value of each voxel of the brain; a PD value of cerebrospinal fluid is taken to be a reference PD value; and the PD value of each voxel of the brain is divided by the reference PD value to obtain the free water content of each voxel of the brain. The method advantageously increases the speed and accuracy of measurement of brain free water content.

11 Claims, 5 Drawing Sheets

(51) Int. Cl.

| | |
|---|---|
| *G01R 33/48* | (2006.01) |
| *G01R 33/50* | (2006.01) |
| *G01R 33/54* | (2006.01) |

(56) References Cited

OTHER PUBLICATIONS

Ma et al. ("Magnetic resonance fingerprinting", Nature, 2013, 495:187-92) hereinafter "Ma" (Year: 2013).*

Neeb et al, a new method of fast quantitative mapping of absolute water content in vivo, Neuroimage, 2006, 1156-68 (Year: 2006).*

Kamman et al. ("Nuclear Magnetic Resonance Relaxation in Experimental Brain Edema: Effects of Water Concentration, Protein Concentration and Water", Magnetic resonance in medicine, 6, 10988 ) (Year: 1988).*

Mezer A et al. "Evaluating Quantitative Proton-Density-Mapping Methods" Human brain mapping, 2016, 37(10): 3623-3635; 2016.

Weiskopf Nikolaus et al: "Unified Segmentation Based Correction of R1 Brain Maps For Rf Transmit Field Inhomogeneities (UNICORT)"; NeuroImage vol. 54; 2011; Elsevier; pp. 2116-2124; 2011.

Shah N J et al. "Quantitative cerebral water content mapping in hepatic encephalopathy" Neuroimage, 2008, 41(3): 706-717; 2008.

Ma D, Gulani V, Seiberlich N, et al. Magnetic resonance fingerprinting. Nature, 2013, 495(7440): 187; 2013.

Ofori E et al. "Longitudinal changes in free-water within the substantia nigra of Parkinson's disease" Brain, 2015, 138(8): 2322-2331; 2015.

* cited by examiner

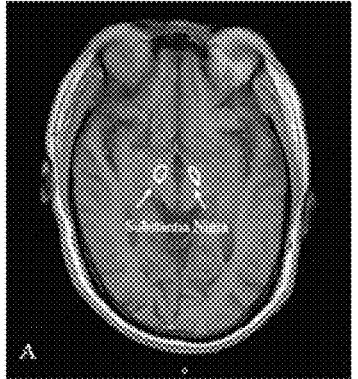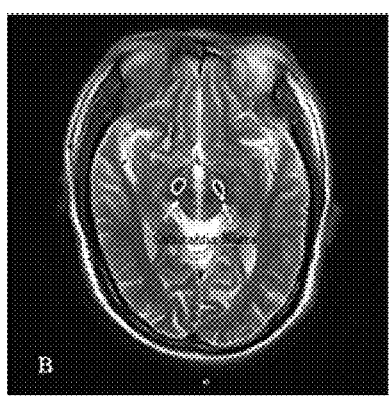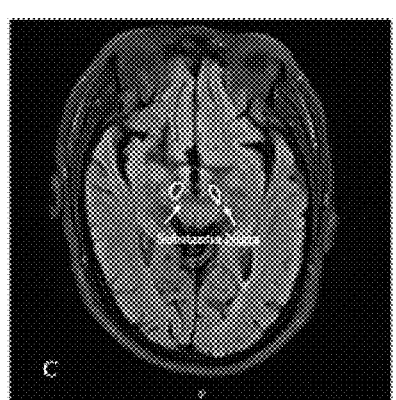
FIG. 1
(related art)

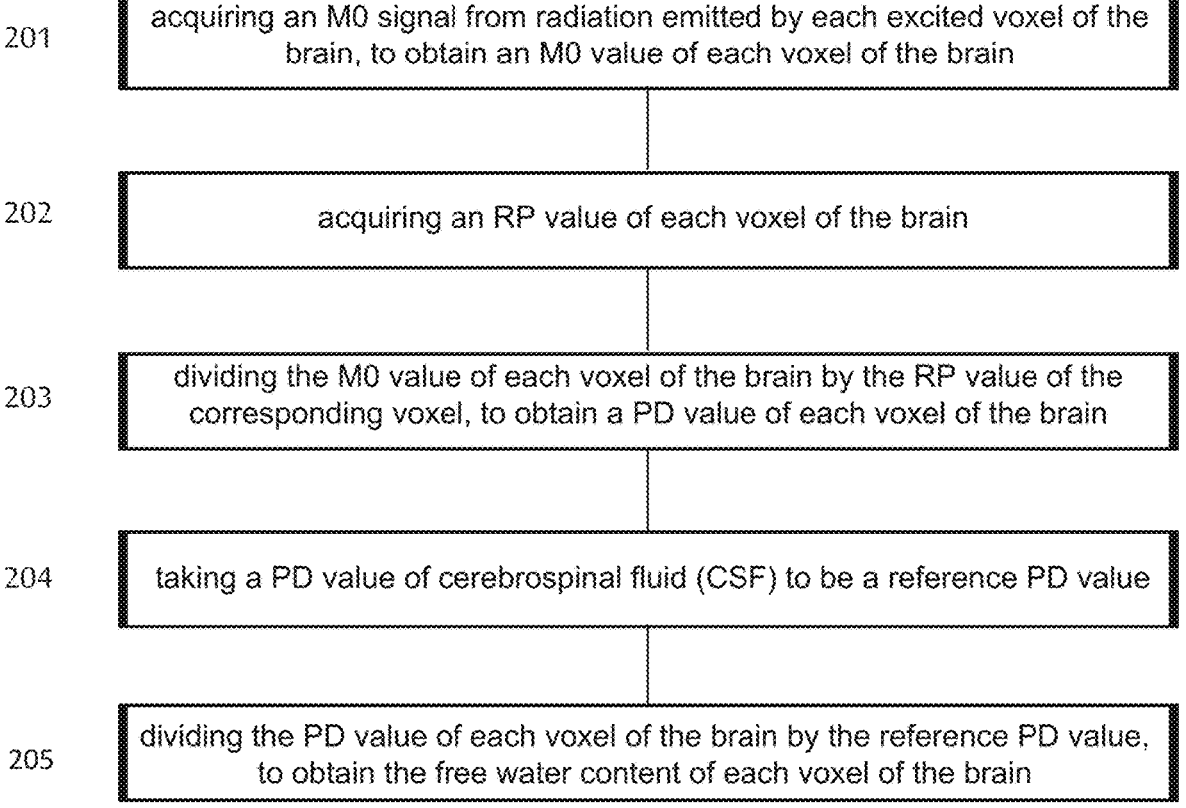

201    acquiring an M0 signal from radiation emitted by each excited voxel of the brain, to obtain an M0 value of each voxel of the brain 202    acquiring an RP value of each voxel of the brain 203    dividing the M0 value of each voxel of the brain by the RP value of the corresponding voxel, to obtain a PD value of each voxel of the brain 204    taking a PD value of cerebrospinal fluid (CSF) to be a reference PD value 205    dividing the PD value of each voxel of the brain by the reference PD value, to obtain the free water content of each voxel of the brain

FIG. 2

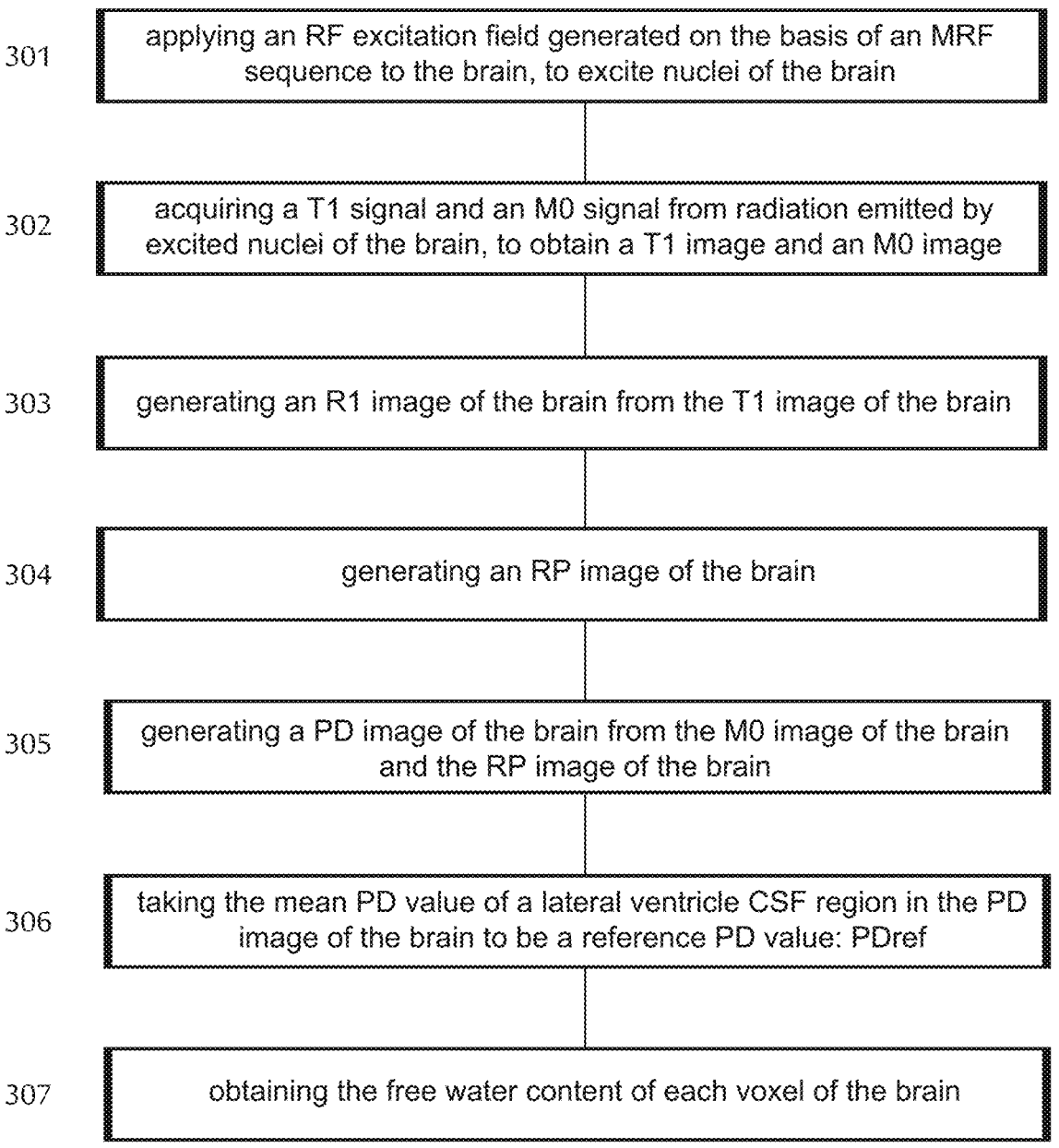

301    applying an RF excitation field generated on the basis of an MRF sequence to the brain, to excite nuclei of the brain 302    acquiring a T1 signal and an M0 signal from radiation emitted by excited nuclei of the brain, to obtain a T1 image and an M0 image 303    generating an R1 image of the brain from the T1 image of the brain 304    generating an RP image of the brain 305    generating a PD image of the brain from the M0 image of the brain and the RP image of the brain 306    taking the mean PD value of a lateral ventricle CSF region in the PD image of the brain to be a reference PD value: PDref 307    obtaining the free water content of each voxel of the brain

METHOD AND APPARATUS FOR MEASURING BRAIN FREE WATER CONTENT AND MRI SYSTEM

CROSS REFERENCE TO RELATED APPLICATIONS

This patent application claims priority to Chinese Patent Application No. 202110878454.9, filed Jul. 30, 2021, which is incorporated herein by reference in its entirety.

BACKGROUND

Field

The present disclosure relates to the technical field of MRI (magnetic resonance imaging), in particular to a method and apparatus for measuring brain free water content and an MRI system.

Related Art

PD (proton density) is a fundamental magnetic resonance (MR) measurement method, representing the characteristic concentration of free water protons in each voxel. Many neurological diseases are accompanied by increased local or global free water content, for example: strokes, brain tumors and hepatic encephalopathy are often linked to brain edema. Although conventional MRI can locate edema, non-quantitative imaging methods lack specificity for normal brain parenchyma, tumor tissue and edema. Knowledge of the correct water content is important in monitoring treatment reactions during treatment of these diseases. The latest research also shows that the free water content in the substantia nigra is a promising biological marker for monitoring the progress of Parkinson's disease, but conventional MRI can only provide limited diagnostic information of value. FIG. 1 shows conventional MRI images of a Parkinson's disease sufferer, wherein A is a T1 (longitudinal relaxation time) weighted image, B is a T2 (transverse relaxation time) weighted image, C is a T1 Flair (fluid-attenuated inversion recovery) image, and the white-circled regions pointed to by the white arrows in A, B and C are the substantia nigra. Thus, the accurate and convenient quantification of the free water content of the human brain is important in researching neurological diseases.

Up till now, MRI-based intra-brain free water content or PD quantitative imaging methods have been proposed. These methods can essentially be divided into the following types:

The first type assumes that PD and T1 have a formulaic relationship, and thereby derives the proton density from a T1 image. However, the use of methods of this type has been limited, because the water contents of different regions of healthy brain tissue differ in terms of their dependence on T1, and differ to an even greater extent under pathological conditions.

The second type uses a combination of multiple sequences to directly determine the parameter M0 (equilibrium magnetization mixed term), and associates M0 in tissue with a corresponding value to determine the water content. Methods of this type can achieve high precision by taking account of multiple correction factors, for example: $T2^*$ effects, transmission field inhomogeneity B1+ and receive coil inhomogeneity. However, methods of this type are restricted by long acquisition times, the need for customized sequences, and complex post-processing, etc., and this has hampered their use in clinical settings.

The third type tries to obtain various bio-physical parameters, such as T1, T2 and PD, based on a single MR sequence acquisition. In methods of this type, a technique known as "MRF (MR Fingerprinting)" can generate accurate T1, T2 and M0 images within a short scan time based on the nature of pattern recognition, but cannot quantify the free water content of the brain directly because M0 is the product of PD and RP (Receiver coil Profile, receiving coil sensitivity).

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 is a conventional MRI image of a Parkinson's disease sufferer.

FIG. 2 is a flowchart of a method for measuring brain free water content according to an exemplary embodiment of the present disclosure.

FIG. 3 is a flowchart of a method for measuring free water content according to an exemplary embodiment of the present disclosure.

Figure 4:
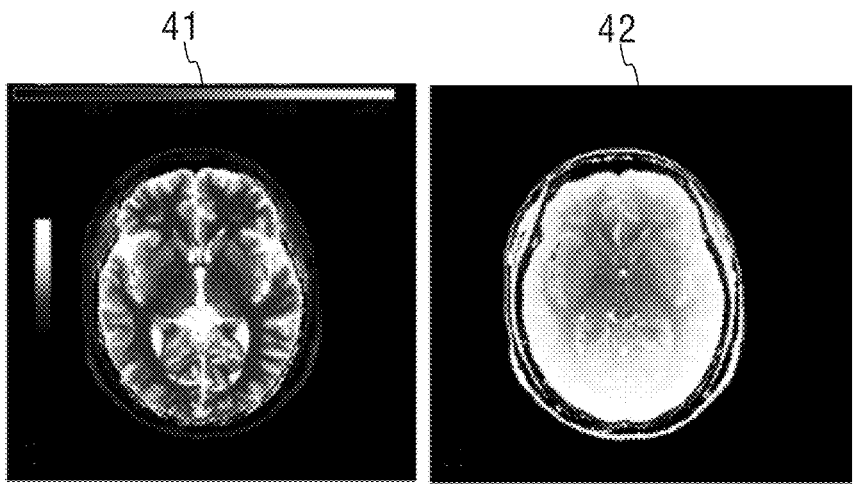
FIG. 4 shows a T1 image and an M0 image of the brain which are acquired using an MRF sequence in an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a method for measuring brain free water content, and additionally propose an apparatus for measuring brain free water content and an MRI system, to increase the speed and accuracy of measurement of the free water content of the brain.

In an exemplary embodiment, a method for measuring brain free water content may include:

in response to an RF excitation field generated on the basis of a magnetic resonance fingerprinting sequence and applied to the brain, acquiring an equilibrium magnetization mixed term (M0) signal from radiation emitted by each excited voxel of the brain, to obtain an M0 value of each voxel of the brain;

acquiring a receive coil sensitivity (RP) value of each voxel of the brain;

dividing the M0 value of each voxel of the brain by the RP value of the corresponding voxel, to obtain a proton density (PD) value of each voxel of the brain;

taking a PD value of cerebrospinal fluid to be a reference PD value;

dividing the PD value of each voxel of the brain by the reference PD value, to obtain the free water content of each voxel of the brain.

The step of taking a PD value of cerebrospinal fluid to be a reference PD value comprises: finding the mean value of the PD values of all voxels of a lateral ventricle cerebrospinal fluid region, and taking the mean value to be the reference PD value.

The step of acquiring an RP value of each voxel of the brain comprises:

in response to an RF excitation field generated on the basis of a sequence for acquiring RP and applied to the brain, acquiring an RP signal from radiation emitted by each excited voxel of the brain, to obtain the RP value of each voxel of the brain.

Concurrently with the step of acquiring an M0 signal from radiation emitted by each excited voxel of the brain, the method further comprises:

acquiring a longitudinal relaxation time (T1) signal from radiation emitted by each excited voxel of the brain, to obtain a T1 value of each voxel of the brain.

The step of acquiring an RP value of each voxel of the brain comprises:

finding the reciprocal of the T1 value of each voxel of the brain, to obtain a measured longitudinal relaxation rate (R1) value of each voxel of the brain;

generating an R1 image of the brain based on the measured R1 values of all voxels of the brain; using a unified segmentation algorithm specifically used for estimating a multiplicative bias between an actual R1 value and the measured R1 value of each voxel of the brain to perform unified segmentation of the R1 image of the brain, to obtain the multiplicative bias between the actual R1 value and the measured R1 value of each voxel of the brain, and taking the multiplicative bias corresponding to each voxel of the brain to be the RP of each voxel of the brain.

In an exemplary embodiment, an apparatus for measuring brain free water content may include: a signal acquisition module for, in response to an RF excitation field generated on the basis of a magnetic resonance fingerprinting sequence and applied to the brain, acquiring an equilibrium magnetization mixed term (M0) signal from radiation emitted by each excited voxel of the brain, to obtain an M0 value of each voxel of the brain;

an RP acquisition module, for acquiring a receive coil sensitivity (RP) value of each voxel of the brain;

a PD acquisition module, for dividing the M0 value of each voxel of the brain by the RP value of the corresponding voxel, to obtain a proton density (PD) value of each voxel of the brain;

and taking a PD value of cerebrospinal fluid to be a reference PD value;

a free water content acquisition module, for dividing the PD value of each voxel of the brain by the reference PD value, to obtain the free water content of each voxel of the brain.

The RP acquisition module acquiring an RP of each voxel of the brain comprises:

in response to an RF excitation field generated on the basis of a sequence for acquiring RP and applied to the brain, acquiring an RP signal from radiation emitted by each excited voxel of the brain, to obtain the RP value of each voxel of the brain.

In an exemplary embodiment, the signal acquisition module may be configured to:

acquire a T1 signal from radiation emitted by each excited voxel of the brain, to obtain a T1 value of each voxel of the brain;

and the RP acquisition module acquiring an RP of each voxel of the brain comprises:

finding the reciprocal of the T1 value of each voxel of the brain, to obtain a measured R1 value of each voxel of the brain; generating an R1 image of the brain based on the measured R1 values of all voxels of the brain; using a unified segmentation algorithm specifically used for estimating a multiplicative bias between an actual R1 value and the measured R1 value of each voxel of the brain to perform unified segmentation of the R1 image of the brain, to obtain the multiplicative bias between the actual R1 value and the measured R1 value of each voxel of the brain, and taking the multiplicative bias corresponding to each voxel of the brain to be the RP of each voxel of the brain.

In an exemplary embodiment, an MRI system may include any one of the apparatuses described above. The MRI system may further include a MR scanner configured to obtain image data from the object under examination.

In an exemplary embodiment, an RF excitation field generated on the basis of an MRF sequence is applied to the brain, the M0 value of each voxel of the brain is acquired, then the PR value of each voxel of the brain is acquired, and based on M0=PD*RP, the PD value of each voxel of the brain is obtained, then the PD value of cerebrospinal fluid is taken to be the reference PD value, and the PD value of each voxel of the brain is divided by the reference PD value, to obtain the free water content of each voxel of the brain. Thus, the acquisition time is short, there is no need to customize the sequence, post-processing is simple, the speed of measurement of the free water content of the brain is increased, quantitative measurement of the free water content of the brain is achieved, and the accuracy of measurement of the free water content of the brain is increased.

FIG. 2 is a flow chart of a method for measuring brain free water content provided in a first embodiment of the present disclosure, specifically having the following steps:

Step 201: in response to an RF excitation field generated on the basis of a magnetic resonance fingerprinting (MRF) sequence and applied to the brain, acquiring an M0 signal from radiation emitted by each excited voxel of the brain, to obtain an M0 value of each voxel of the brain.

Step 202: acquiring an RP value of each voxel of the brain.

Step 203: dividing the M0 value of each voxel of the brain by the RP value of the corresponding voxel, to obtain a PD value of each voxel of the brain.

Step 204: taking a PD value of cerebrospinal fluid (CSF) to be a reference PD value.

In an optional embodiment, the mean value of the PD values of all voxels of a lateral ventricle CSF region is found, and taken to be a reference PD value.

Step 205: dividing the PD value of each voxel of the brain by the reference PD value, to obtain the free water content of each voxel of the brain.

In the above embodiments, an RF excitation field generated on the basis of an MRF sequence is applied to the brain, the M0 value of each voxel of the brain is acquired, then the PR value of each voxel of the brain is acquired, and based on M0=PD*RP, the PD value of each voxel of the brain is obtained, then the PD value of CSF is taken to be the reference PD value, and the PD value of each voxel of the brain is divided by the reference PD value, to obtain the free water content of each voxel of the brain. Thus, the acquisition time is short, there is no need to customize the sequence, post-processing is simple, the speed of measurement of the free water content of the brain is increased, quantitative measurement of the free water content of the brain is achieved, and the accuracy of measurement of the free water content of the brain is increased.

In an optional embodiment, in step 202, the acquisition of the RP value of each voxel of the brain may be performed by one of the following two methods:

Method 1: in response to an RF excitation field generated on the basis of a sequence for acquiring RP and applied to the brain, an RP signal is acquired from radiation emitted by each excited voxel of the brain, to obtain the RP value of each voxel of the brain.

The sequence for acquiring RP is for example: FLASH (Fast Low Angle SHot gradient echo sequence), etc. Method 2: firstly, in step 201, at the same time as acquiring the M0 signal from radiation emitted by each excited voxel of the brain, the method further comprises: acquiring a T1 signal from radiation emitted by each excited voxel of the brain, to obtain a T1 value of each voxel of the brain;

next, finding the reciprocal of the T1 value of each voxel of the brain, to obtain a measured R1 (longitudinal relaxation rate) value of each voxel of the brain;

then generating an R1 image of the brain based on the measured R1 values of all voxels of the brain;

finally, using a unified segmentation algorithm specifically used for estimating a multiplicative bias between an actual R1 value and the measured R1 value of each voxel of the brain to perform unified segmentation of the R1 image of the brain, to obtain the multiplicative bias between the actual R1 value and the measured R1 value of each voxel of the brain, and taking the multiplicative bias corresponding to each voxel of the brain to be the RP of each voxel of the brain.

FIG. 3 is a flow chart of a method for measuring free water content provided in a second embodiment of the present disclosure, specifically having the following steps:

Step 301: applying an RF excitation field generated on the basis of an MRF sequence to the brain, to excite nuclei of the brain.

The first mention of the MRF technique is in the paper "Magnetic Resonance Fingerprinting" in the journal Nature, 2013; the file web address is http://scihub.cc/10.1038/nature11971, and the first author is Dan Ma.

Compared with conventional MRI weighted imaging (e.g. T1 weighted imaging, T2 weighted imaging, PD weighted imaging), the technique has signal uniqueness, and was therefore called "magnetic resonance fingerprinting", similar to a person's fingerprints. The MRF technique is a new method in quantitative MRI, which can measure various tissue attributes, such as T1, T2 and M0, quickly and simultaneously in a single acquisition.

Step 302: acquiring a T1 signal and an M0 signal from radiation emitted by excited nuclei of the brain, to obtain a T1 image and an M0 image of the brain.

The dimensions of the T1 image and the M0 image (i.e. width and height) are exactly the same.

FIG. 4 shows a T1 image and an M0 image of the brain which are acquired using an MRF sequence in an embodiment of the present disclosure, wherein 41 is the T1 image and 42 is the M0 image.

Step 303: based on $R1_{i,j}=1/T1_{i,j}$, generating an R1 image of the brain from the T1 image of the brain.

Here, (i, j) are the position coordinates of any pixel point in the T1 image and R1 image of the brain; i is the coordinate in the width direction, j is the coordinate in the height direction, $0 \leq i \leq M$, $0 \leq j \leq N$, M is the width of the T1 image and R1 image of the brain, and N is the height of the T1 image and R1 image of the brain. $R1_{i,j}$ is the measured R1 value of pixel point (i, j) in the R1 image of the brain, $T1_{i,j}$ is the T1 value of pixel point (i, j) in the T1 image of the brain, and the units of T1 are generally milliseconds.

Thus, the dimensions of the R1 image of the brain and the T1 image of the brain are exactly the same (i.e. the widths and heights are the same), and for any pixel point (i, j) in the R1 image of the brain, the measured R1 value thereof $R1_{i,j}$ satisfies: $R1_{i,j}=1/T1_{i,j}$.

Step 304: using a unified segmentation algorithm specifically used for estimating a multiplicative bias between an actual R1 value and the measured R1 value of each voxel of the brain to perform unified segmentation of the R1 image of the brain, to obtain the multiplicative bias between the actual R1 value and the measured R1 value of each voxel of the brain, and taking the multiplicative bias corresponding to each voxel of the brain to be an RP value of each pixel point in an RP image of the brain, thereby generating an RP image of the brain.

The unified segmentation algorithm was proposed in "Unified segmentation based correction of R1 brain maps for RF transmit field inhomogeneities", published on pages 2116-2124 of Neuroimage, 2011, by Weiskopf N, Lutti A, Helms G et al. The specific information of that article is as follows:

Weiskopf N, Lutti A, Helms G, et al. Unified segmentation based correction of R1 brain maps for RF transmit field inhomogeneities (UNICORT)[J]. Neuroimage, 2011, 54(3): 2116-2124.

The unified segmentation algorithm is used to estimate a multiplicative bias of any type of data having a multiplicative bias. The R1 value of each pixel point in the R1 image of the brain obtained in step 303 is the measured R1 value, and there is a multiplicative bias between the measured R1 value and the actual R1 value, i.e. measured R1 value=actual R1 value*multiplicative bias. The multiplicative bias between the actual R1 value and the measured R1 value of each pixel point can be obtained by using the unified segmentation algorithm to perform unified segmentation of the R1 image of the brain obtained in step 303.

Step 305: based on $PD_{i,j}=M0_{i,j}/RP_{i,j}$, generating a PD image of the brain from the M0 image of the brain and the RP image of the brain.

Here, (i, j) are the position coordinates of any pixel point in the PD image, M0 image and RP image of the brain; i is the coordinate in the width direction, j is the coordinate in the height direction, $0 \leq i \leq M$, $0 \leq j \leq N$, M is the width of the PD image, M0 image and RP image of the brain, and N is the height of the PD image, M0 image and RP image of the brain. $M0_{i,j}$ is the M0 value of pixel point (i, j) in the M0 image of the brain, $RP_{i,j}$ is the RP value of pixel point (i, j) in the RP image of the brain, and $PD_{i,j}$ is the PD value of pixel point (i, j) in the PD image of the brain.

Thus, the dimensions of the PD image, M0 image and RP image of the brain are exactly the same (i.e. the widths and heights are the same), and for any pixel point (i, j) in the PD image of the brain, the PD value thereof $PD_{i,j}$ satisfies: $PD_{i,j} = M0_{i,j}/RP_{i,j}$.

Step 306: taking the mean PD value of a lateral ventricle CSF (cerebrospinal fluid) region in the PD image of the brain to be a reference PD value: $PD_{ref}$.

That is, a lateral ventricle CSF region is first found in the PD image, then the mean value of the PD values of all pixel points in that region is found, and taken to be $PD_{ref}$.

Step 307: based on $FWCnor_{i,j} = PD_{i,j}/PDref$, obtaining the free water content of each voxel of the brain.

Here, $FWCnor_{i,j}$ is the free water content of the voxel corresponding to pixel point (i, j).

Figure 5:
FIG. 5 is a free water content image of the brain obtained by calculation using the method according to an exemplary embodiment of the present disclosure.

FIG. 5 is a free water content image of the brain obtained by calculation using the method provided in an embodiment of the present disclosure.

The above embodiments have the following beneficial technical effects:

Firstly, only one sequence is used: the MRF sequence; the signal acquisition time is short, errors caused by image registration are avoided, and post-processing is simple; thus, the free water content of the brain can be obtained more quickly, and the efficiency is higher, so the method is more suited to clinical applications.

Secondly, because the T1 dependence of the water content under pathological conditions is different from that in a healthy control group, many existing techniques have limitations in clinical applications. This method, on the other hand, uses a unified segmentation algorithm to estimate the multiplicative bias of the R1 image, and thereby obtains RP; the algorithm is effective in many neurodegenerative diseases, so the practical applicability of the method in clinical settings is ensured.

Figure 6:
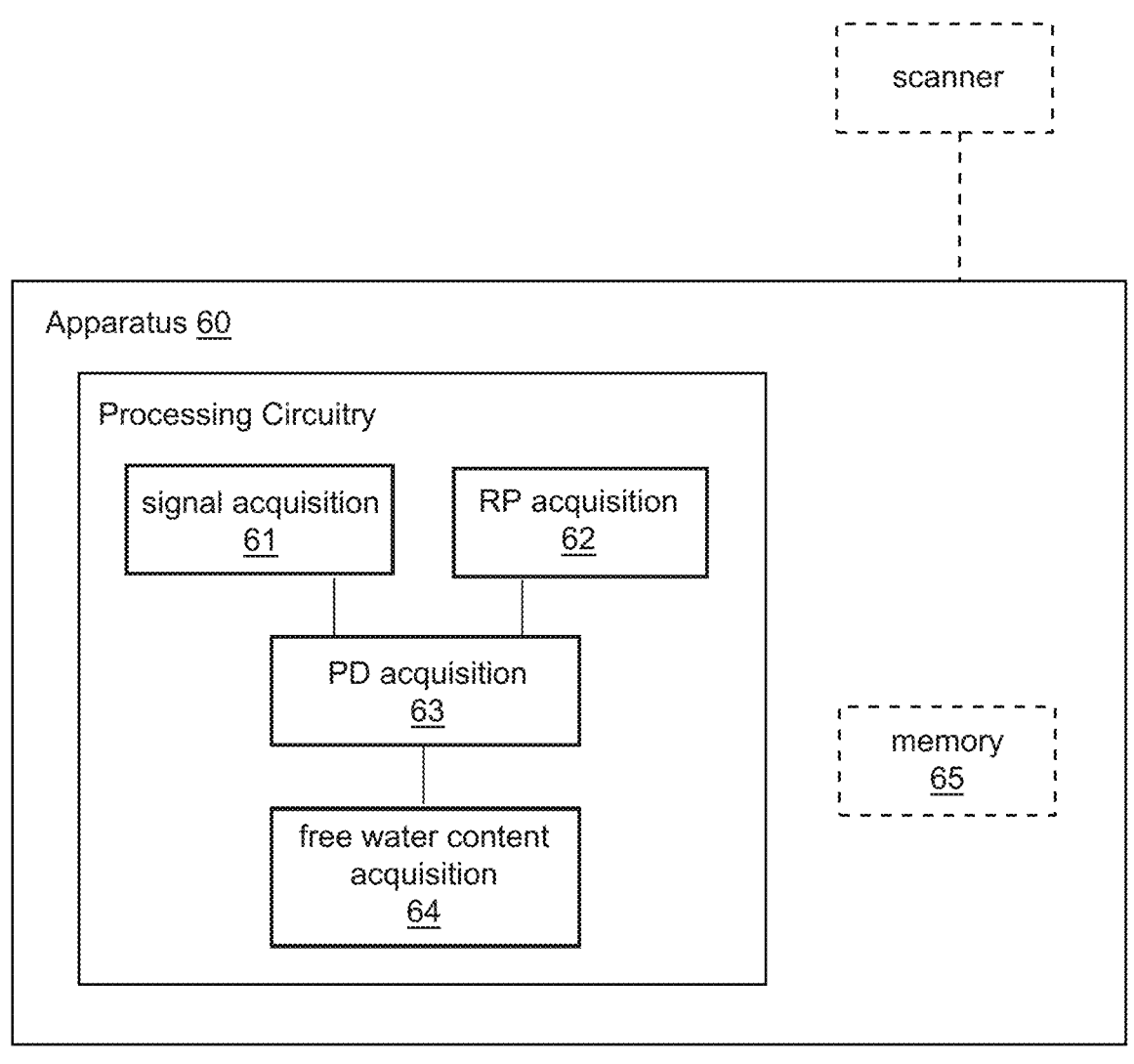
FIG. 6 is an apparatus for measuring brain free water content according to an exemplary embodiment of the present disclosure.

FIG. 6 is a structural schematic diagram of an apparatus 60 for measuring brain free water content according to an exemplary embodiment. The apparatus 60 may include a signal acquisition module 61, RP acquisition module 62, PD acquisition module 63, and free water content acquisition module 64. In an exemplary embodiment, the modules 61-64 are embodied in one or more processors and represent the functions performed by the processor(s) when the processor(s) executes instructions corresponding to the respective functions. As illustrated in FIG. 6, the modules may be embodied by processing circuitry that is configured to perform the functions of the apparatus 60. In an exemplary embodiment, the apparatus 60 may include a memory 65 that may store data and/or executable instructions that is accessible by the processing circuitry and/or one or more modules therein. Additionally, or alternatively, the apparatus 60 may be configured to access one or more external memory units.

In an exemplary embodiment, the signal acquisition module 61 may be configured to, in response to an RF excitation field generated based on an MRF sequence and applied to the brain, acquire an M0 signal from radiation emitted by each excited voxel of the brain, to obtain an M0 value of each voxel of the brain. The RP acquisition module 62 may be configured to acquire an RP value of each voxel of the brain. The PD acquisition module 63 may be configured to divide the M0 value of each voxel of the brain obtained by the signal acquisition module 61 by the RP value of the corresponding voxel acquired by the RP acquisition module 62, to obtain a PD value of each voxel of the brain. The PD acquisition module 63 may additionally or alternatively be configured to take a PD value of CSF to be a reference PD value. The free water content acquisition module 64 may be configured to divide the PD value of each voxel of the brain obtained by the PD acquisition module 63 by the reference PD value obtained by the PD acquisition module 63, to obtain the free water content of each voxel of the brain.

In an exemplary embodiment, the PD acquisition module 63 taking a PD value of CSF to be a reference PD value comprises: finding the mean value of the PD values of all voxels of a lateral ventricle CSF region, and taking the mean value to be the reference PD value.

In an exemplary embodiment, the RP acquisition module 62 acquiring an RP of each voxel of the brain comprises: in response to an RF excitation field generated on the basis of a sequence for acquiring RP and applied to the brain, acquiring an RP signal from radiation emitted by each excited voxel of the brain, to obtain the RP value of each voxel of the brain.

In an exemplary embodiment, the signal acquisition module 61 is further configured to acquire a T1 signal from radiation emitted by each excited voxel of the brain, to obtain a T1 value of each voxel of the brain.

In an exemplary embodiment, the RP acquisition module 62 may be configured to acquire an RP of each voxel of the brain, which comprises: finding the reciprocal of the T1 value of each voxel of the brain obtained by the signal acquisition module 61, to obtain a measured R1 value of each voxel of the brain; generating an R1 image of the brain based on the measured R1 values of all voxels of the brain; using a unified segmentation algorithm specifically used for estimating a multiplicative bias between an actual R1 value and the measured R1 value of each voxel of the brain to perform unified segmentation of the R1 image of the brain, to obtain the multiplicative bias between the actual R1 value and the measured R1 value of each voxel of the brain, and taking the multiplicative bias corresponding to each voxel of the brain to be the RP of each voxel of the brain.

An MRI system proposed in embodiments of the present disclosure may comprise the apparatus for measuring free water content provided in the first or second embodiment above.

The embodiments above are merely preferred embodiments of the present disclosure, which are not intended to limit it. Any amendments, equivalent substitutions or improvements etc. made within the spirit and principles of the present disclosure shall be included in the scope of protection thereof.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

| Reference List | |
|---|---|
| 201-205 | steps |
| 301-307 | steps |
| 41 | T1 image of brain |
| 42 | M0 image of brain |
| 61 | signal acquisition module |
| 62 | RP acquisition module |
| 63 | PD acquisition module |
| 64 | free water content acquisition module |

The invention claimed is:

1. A method for measuring brain free water content, wherein the method comprises:

in response to a radio-frequency (RF) excitation field generated based on a magnetic resonance fingerprinting sequence and applied to the brain, concurrently acquiring, from radiation emitted by each excited voxel of the brain: an equilibrium magnetization mixed term (M0) signal to obtain an M0 value of each voxel of the brain and a longitudinal relaxation time (T1) signal to obtain a T1 value of each voxel of the brain;

acquiring a receive coil sensitivity (RP) value of each voxel of the brain, the acquisition of the RP value of each voxel of the brain comprising:

obtaining a measured longitudinal relaxation rate (R1) value of each voxel of the brain based on a reciprocal of the T1 value of each voxel of the brain;

generating an R1 image of the brain based on the measured R1 values of all voxels of the brain;

determining a multiplicative bias between an actual R1 value and the measured R1 value of each voxel of the brain; and determining the RP value of each voxel of the brain based on the multiplicative bias corresponding to each voxel of the brain;

obtaining a proton density (PD) value of each voxel of the brain based on the M0 value of each voxel of the brain and the RP value of the corresponding voxel;

determining a reference PD value based on a PD value of cerebrospinal fluid;

obtaining the free water content of each voxel of the brain based on the PD value of each voxel of the brain and the reference PD value; and determining free water content data corresponding to the obtained free water content and outputting the free water content data in electronic form as a data file.

2. The method as claimed in claim 1, wherein determining a reference PD value comprises: determining a mean value of the PD values of all voxels of a lateral ventricle cerebrospinal fluid region, the reference PD value being the determined mean value.

3. The method as claimed in claim 1, wherein acquiring the RP value of each voxel of the brain comprises: in response to an RF excitation field generated based on a sequence for acquiring RP and applied to the brain, acquiring an RP signal from radiation emitted by each excited voxel of the brain, to obtain the RP value of each voxel of the brain.

4. The method as claimed in claim 1, wherein determining the multiplicative bias comprises:

estimating the multiplicative bias, using a unified segmentation algorithm specifically used for estimating multiplicative bias between the actual R1 value and the measured R1 value of each voxel of the brain, to perform unified segmentation of the R1 image of the brain.

5. A non-transitory computer-readable storage medium with an executable program stored thereon, that when executed, instructs a processor to perform the method of claim 1.

6. An apparatus for measuring brain free water content, comprising:

a signal acquisition module configured to, in response to a radio-frequency (RF) excitation field generated based on a magnetic resonance fingerprinting sequence and applied to the brain, concurrently acquire, from radiation emitted by each excited voxel of the brain: an equilibrium magnetization mixed term (M0) signal to obtain an M0 value of each voxel of the brain and a longitudinal relaxation time (T1) signal to obtain a T1 value of each voxel of the brain;

a receive coil sensitivity (RP) acquisition module configured to acquire a RP value of each voxel of the brain, the acquisition of the RP value of each voxel of the brain comprising:

obtaining a measured longitudinal relaxation rate (R1) value of each voxel of the brain based on a reciprocal of the T1 value of each voxel of the brain;

generating an R1 image of the brain based on the measured R1 values of all voxels of the brain;

determining a multiplicative bias between an actual R1 value and the measured R1 value of each voxel of the brain; and determining the RP value of each voxel of the brain based on the multiplicative bias corresponding to each voxel of the brain;

a proton density (PD) acquisition module configured to determine a PD value of each voxel of the brain based on the M0 value of each voxel of the brain and the RP value of the corresponding voxel, a PD value of cerebrospinal fluid being a reference PD value; and a free water content acquisition module configured to determine the free water content of each voxel of the brain based on the PD value of each voxel of the brain and the reference PD value.

7. The apparatus as claimed in claim 6, wherein the RP acquisition module acquiring an RP of each voxel of the brain comprises: in response to an RF excitation field generated on the basis of a sequence for acquiring RP and applied to the brain, acquiring an RP signal from radiation emitted by each excited voxel of the brain, to obtain the RP value of each voxel of the brain.

8. The apparatus as claimed in claim 6, wherein the RP acquisition module is configured to determine the multiplicative bias using a unified segmentation algorithm specifically used for estimating the multiplicative bias between the actual R1 value and the measured R1 value of each voxel of the brain to perform unified segmentation of the R1 image of the brain.

9. A magnetic resonance imaging (MRI) system comprising the apparatus as claimed in claim 6.

10. The MRI system according to claim 9, further comprising a scanner configured to obtain MRI data of the brain.

11. An apparatus for measuring brain free water content, comprising:

a memory storing executable instructions; and a processor configured to execute the instructions to cause the apparatus to:

in response to a radio-frequency (RF) excitation field generated based on a magnetic resonance fingerprinting sequence and applied to the brain, concurrently acquire, from radiation emitted by each excited voxel of the brain: an equilibrium magnetization mixed term (M0) signal to obtain an M0 value of each voxel of the brain and a longitudinal relaxation time (T1) signal to obtain a T1 value of each voxel of the brain;

acquire a receive coil sensitivity (RP) value of each voxel of the brain, the acquisition of the RP value of each voxel of the brain comprising:

obtaining a measured longitudinal relaxation rate (R1) value of each voxel of the brain based on a reciprocal of the T1 value of each voxel of the brain;

generating an R1 image of the brain based on the measured R1 values of all voxels of the brain;

determining a multiplicative bias between an actual R1 value and the measured R1 value of each voxel of the brain; and determining the RP value of each voxel of the brain based on the multiplicative bias corresponding to each voxel of the brain;

determine a proton density (PD) value of each voxel of the brain based on the M0 value of each voxel of the brain and the RP value of the corresponding voxel, a PD value of cerebrospinal fluid being a reference PD value; and determine the free water content of each voxel of the brain based on the PD value of each voxel of the brain and the reference PD value.

\* \* \* \* \*